United States Patent [19]
Kwong

[11] Patent Number: 5,702,483
[45] Date of Patent: Dec. 30, 1997

[54] DEBRIS ISOLATING PROSTHETIC HIP JOINT

[76] Inventor: Louis M. Kwong, 9675 Brighton Way, Suite 330, Beverly Hills, Calif. 90210

[21] Appl. No.: 559,480

[22] Filed: Nov. 15, 1995

Related U.S. Application Data

[63] Continuation of Ser. No. 319,437, Oct. 6, 1994, abandoned.
[51] Int. Cl.$^6$ ............... A61F 2/36; A61F 2/32; A61F 2/30
[52] U.S. Cl. ........................ 623/23; 623/18
[58] Field of Search ................ 623/66, 18, 16, 623/22, 23

[56] References Cited

U.S. PATENT DOCUMENTS

| | | |
|---|---|---|
| 3,683,421 | 8/1972 | Martinie. |
| 3,855,638 | 12/1974 | Pilliar ............... 623/26 |
| 4,032,994 | 7/1977 | Frey. |
| 4,166,292 | 9/1979 | Bokros. |
| 4,687,675 | 8/1987 | Nakano et al. ........... 623/22 |
| 4,714,478 | 12/1987 | Fischer. |
| 4,731,088 | 3/1988 | Collier ............... 623/22 |
| 4,743,262 | 5/1988 | Tronzo ............... 623/22 |
| 4,795,471 | 1/1989 | Oh. |
| 4,822,368 | 4/1989 | Collier. |
| 4,888,024 | 12/1989 | Powlan. |
| 4,904,263 | 2/1990 | Buechel et al. ........... 623/23 |
| 5,263,988 | 11/1993 | Huebner. |
| 5,370,698 | 12/1994 | Heimke et al. .......... 623/23 |

FOREIGN PATENT DOCUMENTS

| | | | |
|---|---|---|---|
| 0217034 | 4/1987 | European Pat. Off. ........ | 623/23 |
| 0346294 | 12/1989 | European Pat. Off. ........ | 623/22 |
| 3130732 | 5/1983 | Germany ............... | 623/22 |
| 4211347 | 10/1993 | Germany ............... | 623/22 |

OTHER PUBLICATIONS

Thomas P. Schmalzried, The Journal of Bone and Joint Surgery, vol. 74-A, *Periprosthetic Bone Loss in Total Hip Arthroplasty*, Jul., 1992.

Bobyn et al., 40th Annual Meeting, Orthopaedic Research Society, *The Susceptibility Of Smooth Implant Surfaces To Polyethylene Debris Migration And Per-Implant Fibrosis*, Feb. 21-24, 1994.

Charles A. Engh MD et al., The Journal of Bone and Joint Surgery, *Histological And Radiographic Assessment Of Well Functioning Porous-Coated Acetabular Components*, 1993.

*Primary Examiner*—Debra S. Brittingham
*Attorney, Agent, or Firm*—Plevy & Associates

[57] ABSTRACT

A prosthetic hip assembly comprising an acetabular component having a bearing surface which forms a first articulating surface and a femoral component including a spherically shaped head defining a second articulating surface. The acetabular component includes a first surface treatment for promoting the attachment of fibrous tissue to the acetabular component. The femoral component includes a second surface treatment for promoting the attachment of fibrous tissue to the femoral component. The first and second surface treatments cause fibrous tissue to attach to the femoral component and the acetabular component to form a capsule between the components when the components are implanted in a patient. Any wear debris created by the first and second articulating surfaces rubbing against one another is confined within the capsule to substantially prevent the migration of the wear debris into interfaces between the components and their associated bones. The capsule further operates to substantially prevent metal and cement debris, remaining at the interfaces between the components and their associated bones, from migrating into the fibrous tissue enclosure and toward the articulating surfaces of the components.

18 Claims, 4 Drawing Sheets

DEBRIS ISOLATING PROSTHETIC HIP JOINT

This is a continuation of application Ser. No. 08/319,437, filed on Oct. 6, 1994, entitled DEBRIS ISOLATING PROSTHETIC HIP JOINT, now abandoned.

FIELD OF THE INVENTION

The present invention relates generally to a prosthetic hip joint assembly, and more particularly to a prosthetic hip joint assembly which has been adapted to promote the formation of a fibrous capsule of tissue which seals and encapsulates the prosthetic hip joint.

BACKGROUND OF THE INVENTION

The natural hip joint consists of a ball-like member called the femoral head which is attached to the proximal end of the femur by a neck member, the femoral head being rotatable in a socket like cavity known as the acetabulum which forms a portion of the pelvis. Deterioration of the acetabulum and/or femoral head can be brought about by injury or various progressive diseases such as osteoarthritis. When injury or disease occurs, the damaged components can be replaced or rebuilt via total hip arthroplasty.

Total hip arthroplasty involves replacing the femoral head and neck with a prosthesis which comprises a head, a neck and an elongated stem which is implanted into the medullary canal within the proximal femur. Also replaced in a total hip arthroplasty is the corresponding artificial socket member or acetabular cup, that is fitted into the acetabulum, which may be suitably enlarged for this purpose.

Acetabular cup assemblies typically comprise a metal or plastic cup shell which is adapted to be secured within the patient's acetabulum. Disposed within the cup shell is an inner liner of plastic material made from ultra high-density polyethylene, which provides a spherical bearing surface for receiving the articulating head member of the implanted femoral component. The head member of the implanted femoral component may comprise a cobalt/chromium alloy or be a ceramic such as zirconia.

Two particular problems that are associated with this prosthesis. The first problem involves the generation of polyethylene wear debris by the articulating surfaces of the acetabular and femoral components rubbing against one another. The wear debris migrates toward the boundary of the bone preparation and into the interfaces of the implant and bone thereby causing macrophage-mediated osteolysis. Osteolysis results in trauma and pain to the patient and is known to lead to eventual implant loosening which requires removal and replacement of the implant to avoid catastrophic failure of the prosthesis.

The second problem associated with the above described prosthesis involves the metal and cement particles which are left behind at the interfaces of the implants and bones after surgery. These particles can migrate toward the articulating surfaces of the implants and prematurely wear the bearing surfaces of the implant components which in turn increases the serverity of wear debris and the problems associated therewith. A more in-depth discussion of these problems can be found in an article entitled PERIPROSTHETIC BONE LOSS IN TOTAL HIP ARTHROPLASTY by Thomas P. Schmalzried et al., and published in The Journal of Bone and Joint Surgery, Vol 74-A, July 1992.

The prior art includes devices which are specifically designed to solve the first problem described above by providing various methods for isolating the wear debris. In U.S. Pat. No. 3,683,421 entitled PROSTHETIC JOINT ASSEMBLY, issued to Martinie on Aug. 15, 1972, an encapsulated prosthetic hip Joint assembly is described. In the Martinie patent, the bearing is mechanically sealed. In particular, a flexible cover is employed to surround the hip joint assembly to retain a lubricating fluid around the joint to lubricate it and segregate any wear debris from the body tissues.

A prosthetic hip joint assembly that lubricates the wear surfaces of the joint with a reservoir of lubricant obtained from the scar tissue which forms post-operatively around the hip joint is described in U.S. Pat. No. 4,032,994 entitled HIP JOINT PROSTHESIS, issued to Frey on Jul. 5, 1977. In the Frey patent, scar tissue envelopes the entire bearing but simply contacts the acetabular and femoral components without attaching directly to them.

U.S. Pat. No. 4,822,368 entitled SURGICAL METHOD OF ATTACHING ENCLOSURE MEMBER FOR PROSTHETIC JOINT, issued to Collier on Apr. 18, 1989, describes a flexible enclosure which is attached to both the femoral and acetabular components of prosthetic Joint assembly to isolate wear debris.

The aforementioned devices have been less than successful for various reasons. Hence, the problems described above remain unsolved by the prior art.

Recently, the literature has reported findings which suggest that porous surfaces formed on prosthetic components may be more resistant to polyethylene migration. In an article entitled THE SUSCEPTIBILITY OF SMOOTH IMPLANT SURFACES TO POLYETHYLENE DEBRIS MIGRATION AND PERI-IMPLANT FIBROSIS, presented at the 40th Annual Meeting, Orthopaedic Research Society, on Feb. 21–24, 1994, in New Orleans, La. by J. D. Bobyn et al., the authors reported that smooth implant surfaces are more susceptible to polyethylene debris ingress and debris-mediated fibrosis when compared to porous implant surfaces, that cystic lesions around uncemented femoral components develop preferentially adjacent to smooth implant surfaces and that fibrous tissue containing polyethylene particles forms preferentially adjacent to non-porous coated regions of uncemented hip stems.

In another article entitled HISTOLOGICAL AND RADIOGRAPHIC ASSESSMENT OF WELL FUNCTIONING POROUS-COATED ACETABULAR COMPONENTS, by Charles A. Engh MD et al. and published in 1993 in The Journal of Bone and Joint Surgery, the authors reported on nine porous-coated acetabular components and found that the bone ingrowth promoted by the porous coating, although incomplete across the porous surface of the component, resulted in the presence of fibrous tissue in the non-ossified areas which apparently prohibited the deposit of particulate debris.

It is, therefore, a primary object of the present invention to provide an improved prosthetic hip joint comprising surface treatments on selected areas of the femoral and acetabular components which promote the attachment of a fibrous tissue enclosure between the aforesaid components which operates to seal and encapsulate the prosthetic hip joint.

SUMMARY OF THE INVENTION

A prosthetic hip assembly which comprises an acetabular component having a first articulating surface and a femoral component having a second articulating surface. The acetabular component comprises first surface treatment means for promoting the attachment of fibrous tissue to the acetabular component. The femoral component comprises second surface treatment means for promoting the attachment of fibrous tissue to the femoral component. Hence, fibrous tissue which attaches to the first and second means when the hip assembly is implanted in a patient, forms a capsule between the components. The wear debris created by the first and second articulating surfaces rubbing against one another is confined within the capsule to substantially prevent the migration of the wear debris into interfaces between the components and their associated bones. The capsule further operates to substantially prevent metal and cement debris, remaining at the interfaces between the components and their associated bones, from migrating into the fibrous tissue enclosure and toward the articulating surfaces of the components.

DETAILED DESCRIPTION OF THE INVENTION

Figure 1A:
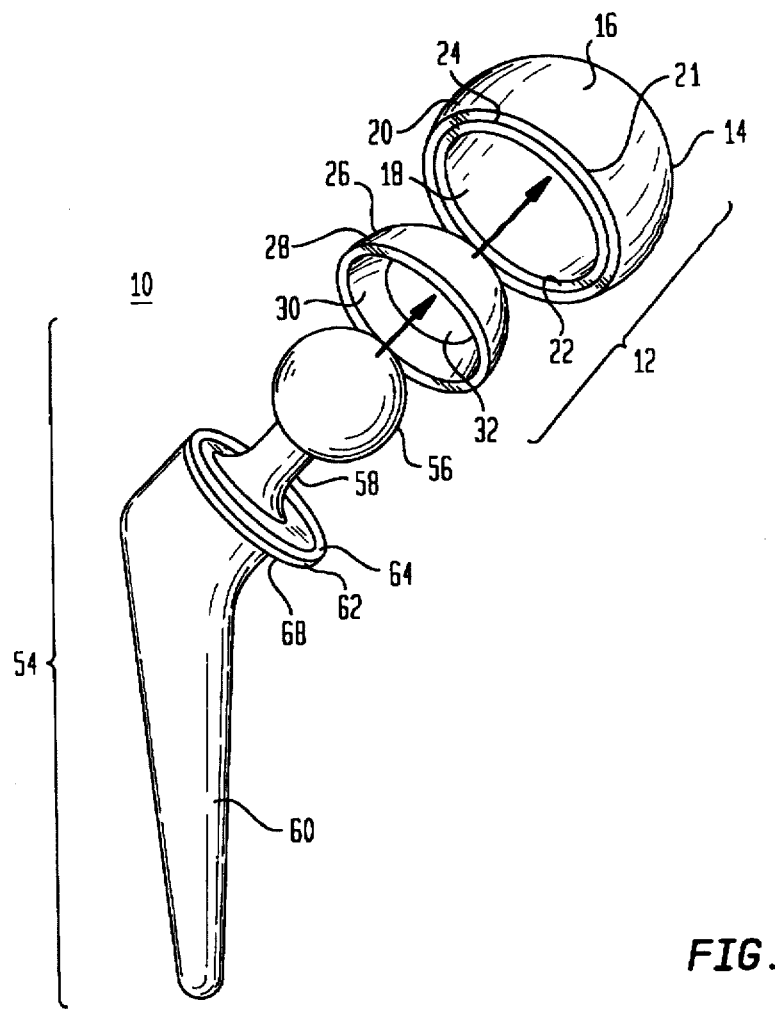
FIG. 1A is a exploded perspective view of an exemplary embodiment of the prosthetic hip joint assembly of the present invention.

Referring to FIG. 1A, there is shown an exemplary preferred embodiment of a prosthetic hip joint assembly according to the present invention designated by the numeral 10. Generally, the hip joint 10 is a two component assembly comprising an acetabular component 12 and a femoral component 54.

The acetabular component 12 of the hip prosthesis 10 is dimensioned to be press-fitted or cemented within acetabulum of the pelvis. The acetabular component comprises a shell 14 and a bearing insert disposed within the hollow of the shell 14. Preferably, the shell 14 is manufactured from a metal such as titanium, chrome molybdenum, stainless steel or any other material such as plastic which is compatible with the bone and body tissues of the patient. The bearing insert 26 is preferably made from a plastic material such as polyethylene or any other like bio-compatible bearing material which has sufficient strength, abrasive resistance and rigidity.

The shell 14 has a generally hemispherical exterior surface 16 and a generally hemispherical interior surface 18 which defines the hollow of the shell 14. The bearing insert 26 is disposed within the hollow of the shell 14 and includes a generally hemispherical exterior surface 28 which is adapted to conform with the interior surface 18 of the shell 14. The interior surface 30 of the bearing insert 26 is generally hemispherical in shape and includes an articular surface region 32.

The marginal end of the shell 14 defines a base region 20. The base region 20 of the shell 14 terminates at an annular rim 21 which defines a surface 22. Preferably, the surface 22 of the annular rim 21 includes a groove 23 for containing a surface treatment 24 as best shown in FIG. 1B. It should be understood, however, that the groove 23 can be omitted depending on the type of surface treatment employed. In any event, a surface treatment 24 is provided on or in the surface 22 of the annular rim 21 for the purpose of promoting the attachment of fibrous tissue to the annular rim 21 of the shell 14. The details of the surface treatment will be described in greater detail below.

Figure 2A:
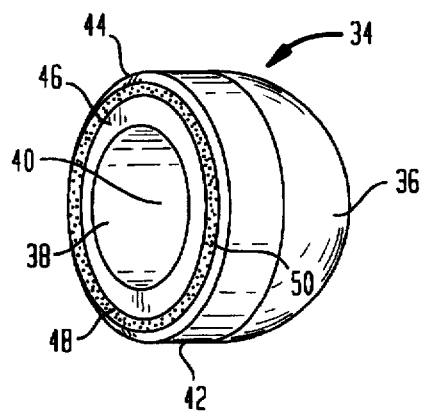
FIG. 2A is a perspective view of a second exemplary embodiment of the acetabular component of the present invention.

The acetabular component can also be comprised as a single unitary cup 34 as shown in the embodiment of FIG. 2A. The acetabular component of this embodiment can be manufactured from plastic or from metal. The exterior surface 36 and interior surface 38 are both generally hemispherical in shape. The interior surface 38 includes an articular surface region 40. The marginal end of the cup 34 defines a base region 42. The base region 42 of the cup 34 terminates at an annular rim 44. The surface 46 of the annular rim 44 is configured in the same way as shown by acetabular component of FIG. 1A and can include an optional groove 48 containing a surface treatment 50.

Figure 2B:
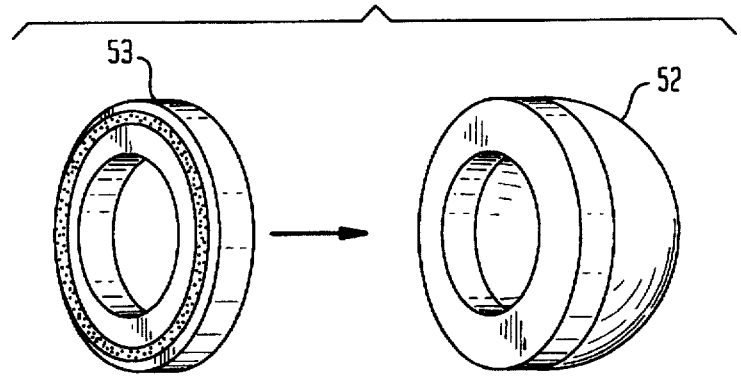
FIG. 2B is a perspective view of a third exemplary embodiment of the acetabular component of the present invention.

A third embodiment of the acetabular component is shown in FIG. 2B. This embodiment is similar to the embodiment shown in FIG. 2A except that the surface treatment is formed, as earlier described, on a separately attached metal or plastic ring 53 which forms the base of the cup. The ring 53 can be attached to the upper portion 52 of the cup using any suitable method. The upper portion of the cup can be manufactured from metal or plastic.

Referring again to FIG. 1A, the femoral component 54 of the hip prosthesis 10 is dimensioned to be press-fitted or cemented within a bore formed in the femoral intramedullary canal. The femoral component 54 can be manufactured from titanium alloy, cobalt-chromium alloy or any other suitable material well known in the art.

The femoral component 54 preferably comprises a spherically shaped head 56, a neck 58, an elongated stem 60 joined to the head 56 by the neck 58, and may have a collar 62 around the neck 58 near its juncture with the stem 60. The head 56 presents a generally spherical surface which articulates against the articular surface region 32 of the bearing insert 26.

Figure 1C:
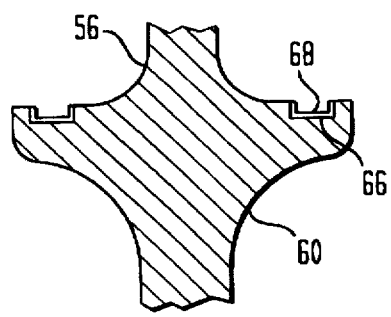
FIG. 1C is a cross-sectional view through the femoral component of FIG. 1A.
Figure 1B:
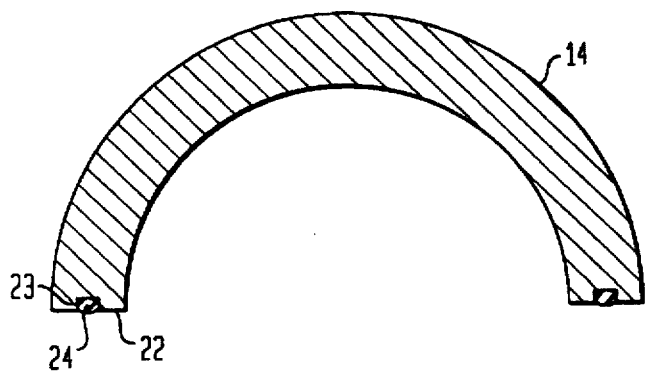
FIG. 1B is a cross-sectional view though the shell of the acetabular component of FIG. 1A.

As best seen in FIG. 1C, the collar 62 defines a surface 64. Preferably, the surface 64 of the collar 62 is arranged in a manner similar to surface 22 of the acetabular component as earlier described. Thus, the surface 64 of the collar 62 preferably includes a groove 66 for containing a surface treatment 68. This groove 66 can be omitted, however, depending on the type of surface treatment employed as long as the surface treatment 68 is provided on or in the surface 64 of the collar 62. The surface treatment 68, which will be describe in greater detail below, is provided for the purpose of promoting the attachment of fibrous tissue to the femoral component.

Figure 3:
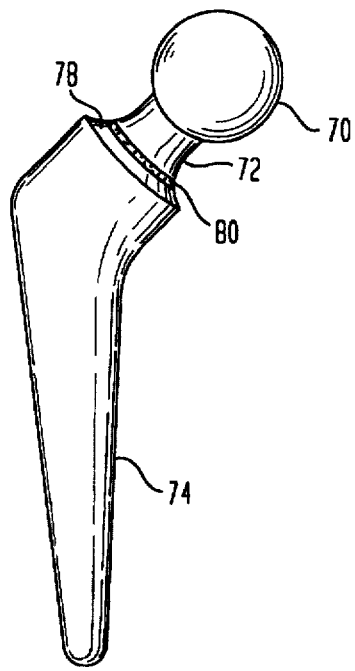
FIG. 3 is a perspective view of an alternative exemplary embodiment of the femoral component of the present invention.

An alternative embodiment of the femoral component is shown in FIG. 3. In this embodiment the femoral component comprises a head 70, a neck 72, and an elongated stem 74 joined to the head 70 by the neck 76. The femoral component of this embodiment differs from the femoral component shown in FIG. 1A in that it does not include a collar around the neck near its juncture with the stem. Hence, the surface treatment 80 in this embodiment of the femoral component is provided at the base of the neck 78.

The novel surface treatments provided on both the acetabular and femoral components will now be described. Generally, any surface treatment that causes the fibrous tissue to sealingly attach to the selected surfaces of the implanted components is intended to be within scope of the present invention. Such surface treatments can take the form of mechanical, chemical, or mechanical/chemical surface treatments. The preferred surface treatment comprises a porous surface on each component. The porous surface provided on each component promotes the ingrowth and attachment of fibrous tissue to the implanted components.

Preferably, the porous surface is provided by a separately applied material which is bonded to the selected surfaces of the acetabular and femoral components. The preferred choice of material comprises a plurality of beads which can be made from any suitable bio-compatible material such as cobalt chromium. The beads are applied to the earlier described surfaces of the acetabular and femoral components which have been selected for surface treatment. After the beads are applied, they are then sintered to permanently bond the beads to the components. The beads can be applied in a single layer or in multiple layers and the layers themselves can be composed of different materials. As is well known, the spaces between the beads form the desired pore spaces.

A composite of wire mesh is another example of a material which can be applied and bonded to the acetabular and femoral components to form a porous surface. Wire meshes are presently used in the art to aid in securing prosthetic devices within their associated bones. As used in the present invention, the spaces of the mesh provide the desired pore spaces for fibrous tissue attachment.

Alternatively, the porous surface can be created by various methods which provide a porous surface directly in the selected surfaces of the acetabular and femoral components. The pores that are provided can extend completely through these selected surfaces or have a predetermined depth. Such pores can be created by micro-machining using chemical etching, laser or any other like manufacturing method.

Whether the porous surface is provided by beads or micro-machining, the pores should be configured to promote fibrous tissue ingrowth into the pores rather than bone ingrowth. This is accomplished by maintaining a pore size diameter of between 25 and 500 microns.

As alternative to a porous surface, the surface treatment can take the form of a ceramic bio-active coating applied to the aforesaid surfaces of the acetabular and femoral components. The bio-active coating causes fibrous tissue to attach to the coated surfaces of the implanted components. The bonding mechanism associated with a bio-active coating is generally chemical in nature although the micro-porosity of the ceramic offers some mechanical bonding.

Bio-active coatings generally comprise a ceramic material having at least one artificial apatite or Calcium Phosphate. Such coatings are well known and include hydroxyapatite $(Ca_{10}(PO_4)_6 (OH)_2)$; fluorapatite $(Ca_{10}(PO_4)_6 (F)_2)$; tricalcium phosphate $(Ca_3(PO_4)_2)$ or any other well known artificial apatite.

When sintered beads or a bio-active coating is chosen as the surface treatment, it is preferred that these types of surface treatments be contained within the earlier described grooves formed in the selected surfaces of the acetabular and/or femoral components. This reduces the chance of shearing the beads or bio-active coating from the surface of the component. The aforementioned groove is not required, however, if a micro-machined porous surface is employed.

One of ordinary skill in the art will recognize that the surface treatments provided on the acetabular and femoral components needn't be identical. For example, the surface treatment on the acetabular component can comprise the sintered beads while the surface treatment provided on the femoral component can comprise the micro-machined pores.

Figure 4:
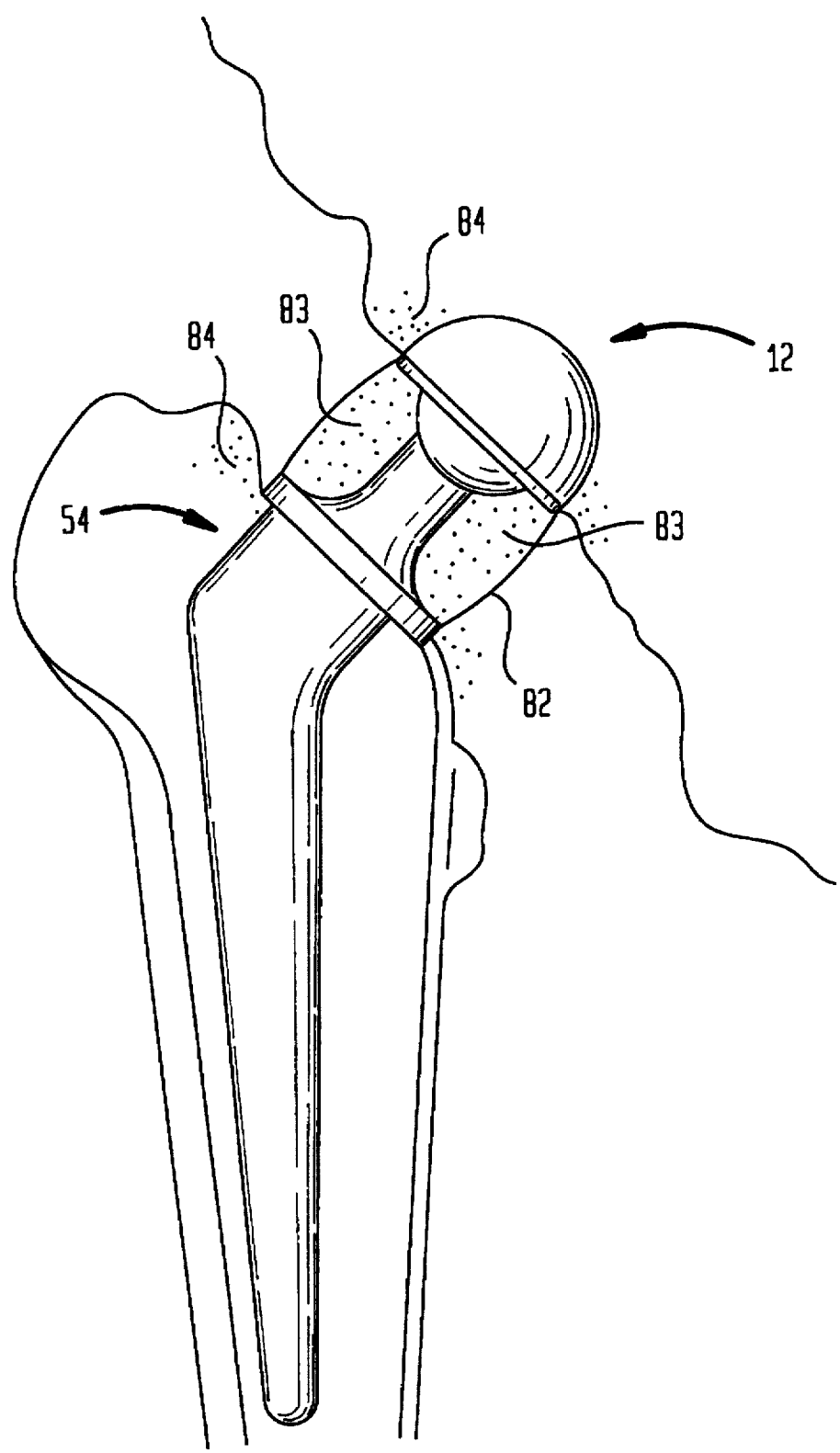
FIG. 4 is a partial cross-sectional view showing the prosthetic hip joint of FIG. 1A implanted in a patient.

Referring to FIG. 4, the implanted femoral 54 and acetabular 12 components of FIG. 1 are shown situated such that the rim surface 22 of the acetabular cup is oriented in opposing relation with the surface 64 of the collar 62 (or the shoulder depending upon the type of femoral component used) of the femoral component 54. The surface treatments on the opposing surfaces promote the attachment of fibrous tissue to the acetabular and femoral components. The fibrous tissue, when fully developed, extends between the surface of the collar or base of the neck of the femoral component and the surface of annular rim of the acetabular cup thereby forming a substantially sealed capsule 82.

Any wear debris 83 resulting from the rubbing together of the aforesaid articulating surfaces is confined within the capsule 82 and away from the boundary of the bone preparation. Thus, wear debris is substantially prevented from migrating toward the interfaces between the implant components and their associated bone tissues. Accordingly, wear debris promoted osteolysis and its resulting trauma, pain and potential for implant loosening is reduced. The capsule 82 further operates to substantially prevent metal and cement debris 84, remaining at the interfaces between the components and their associated bones, from migrating into the capsule and toward the articulating surfaces of the components.

Figure 5:
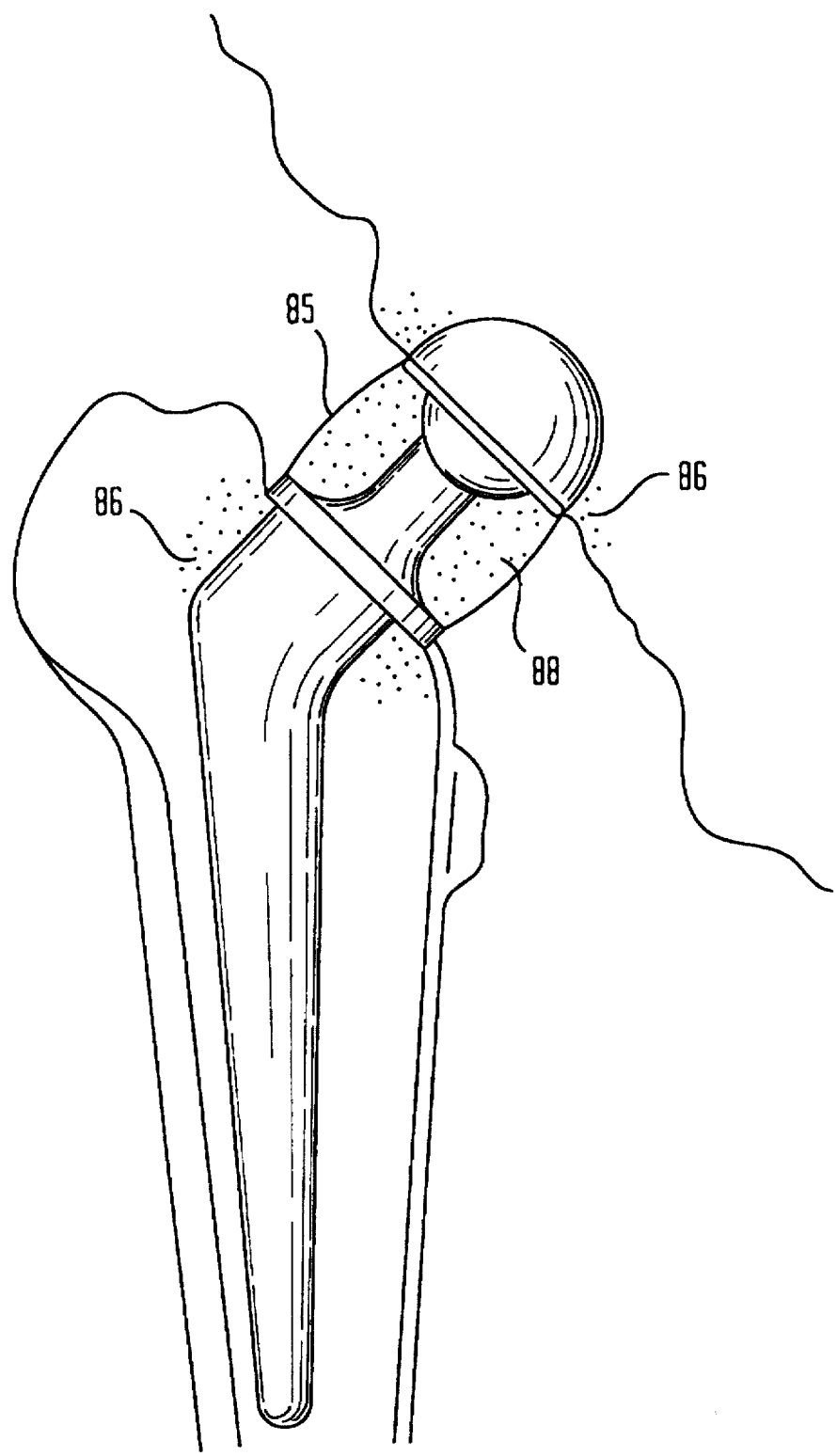
FIG. 5 is a partial cross-sectional view showing a prior art prosthetic hip joint implanted in a patient.

This is in marked contrast to the prior art prosthetic hip joint assembly shown in FIG. 5, which shows the formation of a normal capsule 85 of fibrous tissue. Since the prior art acetabular and femoral components lack the surface treatments of the present invention, the fibrous tissue tends to attach within the boundary of the bone preparation circumscribing the acetabular component and the femoral component. Consequently, any wear debris 86 from the bearing insert can easily migrate toward the preparation boundary into the interfaces between the implants and adjacent bone producing osteolysis and eventual implant loosening. Moreover, metal and cement debris 88, remaining at the interfaces between the components and their associated bones, can easily migrate into the capsule and toward the articulating surfaces of the components and cause premature bearing wear and additional wear debris.

Although the exemplary embodiments of the prosthetic hip assembly described above are designed to replace the human hip, modifications of these devices to render them suitable in other applications such as the shoulder or the knee, will become apparent to those skilled in the art. Moreover, the surface treatments may be located anywhere on the acetabular and femoral components as long as the fibrous capsule of tissue formed therebetween extends within the preparation boundary between the implants and adjacent bone thereby forming a sealed enclosure.

Thus, these and other variations or modifications to the invention described herein are intended to be included within the scope of the invention as defined by the appended claims.

I claim:

1. In a prosthetic hip assembly of the type including an acetabular component comprising a generally hemispherical exterior surface and a generally hemispherical interior surface, said interior surface defining a first articulating surface, and a continuous annular rim surface extending radially from said interior surface to said exterior surface, and a femoral component comprising an elongated stem, a neck extending from said stem, and a spherically shaped head coupled to a free end of said neck, said head defining a second articulating surface, the improvement therewith comprising:

first surface treatment means forming a portion of said continuous annular rim surface for promoting the attachment of a fibrous tissue to said acetabular component, said first surface treatment means extending entirely along said continuous annular rim surface; and second surface treatment means for promoting the attachment of the fibrous tissue to said femoral component, said surface treatment means forming a continuous annular portion of a surface of said femoral component which is located adjacent to said neck, wherein said surface having said second surface treatment means faces substantially toward said spherically shaped head and said first surface treatment means being in opposing relationship with said second surface treatment means when said components are implanted into selected bones of a patient, wherein the fibrous tissue attaching to said first and second means forms a sealed capsule between said components, whereby said sealed capsule substantially prevents wear debris, created within said capsule by said first and second articulating surfaces rubbing against one another, from migrating out of said sealed capsule into interfaces between said components and said selected bones and substantially prevents metal and cement debris, remaining at the interfaces between said components and said selected bones after said implantation from migrating into said sealed capsule and toward said first and second articulating surfaces.

2. The prosthetic hip assembly according to claim 1, wherein at least one of said first and second surface treatment means comprises a bio-active coating.

3. The prosthetic hip assembly according to claim 1, wherein at least one of said first and second means comprises a porous structure.

4. The prosthetic hip assembly according to claim 3, wherein said porous structure comprises at least one layer of beads made from a bio-compatible material.

5. The prosthetic hip assembly according to claim 3, wherein said porous structure comprises a plurality of pores formed in at least one of said surfaces of said femoral component and said annular rim surface of said acetabular component.

6. The prosthetic hip assembly according to claim 3, wherein said porous structure includes pores which range in diameter from between 25 and 500 microns.

7. A prosthetic acetabular cup comprising:

an acetabular component having a generally hemispherical exterior surface, a generally hemispherical interior surface, and a continuous annular rim surface extending radially from said interior surface to said exterior surface; and surface treatment means forming a portion of said continuous annular rim surface for promoting the attachment of fibrous tissue thereto, said surface treatment means extending entirely along said continuous annular rim surface.

8. The prosthetic acetabular cup according to claim 7, wherein said surface treatment means comprises a porous structure.

9. The prosthetic acetabular cup according to claim 8, wherein said porous surface comprises at least one layer of beads disposed on said annular rim surface.

10. The prosthetic acetabular cup according to claim 8, wherein said porous surface comprises a plurality of pores formed in said annular rim surface.

11. The prosthetic acetabular cup according to claim 8, wherein said porous structure includes pores which range in diameter from between 25 and 500 microns.

12. The prosthetic acetabular cup according to claim 7, wherein said surface treatment means comprises a bio-active coating.

13. A femoral prosthetic device comprising:

an elongated stem;

a neck extending from said stem;

a spherically shaped head coupled to a free end of said neck; and surface treatment means for promoting the ingrowth of fibrous tissue, said surface treatment means forming a continuous annular portion of a surface which is located adjacent to said neck, wherein said surface and said surface treatment means faces substantially toward said spherically shaped head.

14. The femoral prosthetic device according to claim 13, wherein said surface treatment means comprises a porous structure.

15. The femoral prosthetic device according to claim 14, wherein said porous structure is at least one layer of bio-compatible beads disposed on said surface located adjacent to said neck.

16. The femoral prosthetic device according to claim 14, wherein said porous structure comprises a plurality of pores formed in said surface located adjacent to said neck.

17. The femoral prosthetic device according to claim 14, wherein said porous structure includes a plurality of pores which range in diameter from between 25 and 500 microns.

18. The femoral prosthetic device according to claim 14, wherein said surface treatment means comprises a bio-active coating.

\* \* \* \* \*